United States Patent
Lu

(10) Patent No.: US 11,066,929 B2
(45) Date of Patent: Jul. 20, 2021

(54) IDENTIFYING OIL AND GAS RESERVOIRS WITH OXYGEN ISOTOPES

(71) Applicant: Saudi Arabian Oil Company, Dhahran (SA)

(72) Inventor: Feng Hu Lu, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 214 days.

(21) Appl. No.: 16/046,095

(22) Filed: Jul. 26, 2018

(65) Prior Publication Data

US 2019/0055842 A1    Feb. 21, 2019

Related U.S. Application Data

(60) Provisional application No. 62/545,637, filed on Aug. 15, 2017.

(51) Int. Cl.
| | | |
|---|---|---|
| *E21B 49/02* | (2006.01) | |
| *E21B 49/00* | (2006.01) | |
| *G01N 33/24* | (2006.01) | |
| *G01V 9/00* | (2006.01) | |
| *G01V 11/00* | (2006.01) | |

(52) U.S. Cl.
CPC .............. *E21B 49/02* (2013.01); *E21B 49/00* (2013.01); *G01N 33/241* (2013.01); *G01V 9/007* (2013.01); *G01V 11/005* (2013.01)

(58) Field of Classification Search
CPC ......... E21B 49/02; E21B 49/00; G01V 9/007; G01N 33/241; G01N 33/24
See application file for complete search history.

(56) References Cited

U.S. PATENT DOCUMENTS

| | | |
|---|---|---|
| 2,874,565 A | 2/1959 | Kelton |
| 5,241,859 A | 9/1993 | Smith |
| 5,359,194 A | 10/1994 | Moss |

OTHER PUBLICATIONS

Wang et al., Raman Geothermometry of Carbonaceous Material in the Basal Ediacaran Doushantuo Cap Dolostone: The Thermal History of Extremely Negative δ13C Signatures in the Aftermath of the Terminal Cryogenian Snowball Earth Glaciation, Online Jun. 13, 2017, Precambrian Research 298, pp. 174-186 (Year: 2017).*

(Continued)

*Primary Examiner* — Toan M Le
(74) *Attorney, Agent, or Firm* — Fish & Richardson P.C.

(57) ABSTRACT

Carbonate samples are received from a wellbore formed in a geologic formation. An oxygen isotope ratio and carbon isotope ratio present within each of the carbonate samples are determined. A mineral composition of each of the carbonate samples is determined. A plot showing the determined oxygen isotope ratios versus a depth from where within the wellbore each of the carbonate samples was obtained is created. One or more negative oxygen isotope shifts are identified based on the plot. Natural carbonate cement levels within one or more of the plurality of carbonate samples that correspond to the one or more negative oxygen isotope shifts identified in the plot are determined. One or more production sweet spots are determined based on the identified negative oxygen isotope shifts and the determined natural carbonate cement levels.

11 Claims, 3 Drawing Sheets

(56) References Cited

OTHER PUBLICATIONS

De Wit et al., "Multiple Organic Carbon Isotope Reversals across the Permo-Triassic Boundary of Terrestrial Gondwana Sequences: Clues to Extinction Patterns and Delayed Ecosystem Recovery," The Journal of Geology 110, No. 2, Mar. 2002, 21 pages.

Jarvis et al., "Secular variation in Late Cretaceous carbon isotopes: a new 13C carbonate reference curve for the Cenomanian-Campanian (99.6--70.6 Ma)," Kingston University London, Geological Magazine, vol. 143, No. 5, Sep. 2006, 49 pages.

Retallack and Jahren, "Methane Release from Igneous Intrusion of Coal during Late Permian Extinction Events," University of Oregon, Eugene Oregon, the Journal of Geology, vol. 116, Issue 1, Jan. 2008, 21 pages.

Tavakoli et al., "Diagenetic controlled reservoir quality of South Pars gas field, and integrated approach," Comptes Rendus—Geoscience, Elsevier, Paris, France, vol. 343, No. 1, Oct. 5, 2010, 17 pages.

Hitzman et al., "Routine staining of drill core to determine carbonate mineralogy and distinguished carbonate alteration textures," Mineralium Deposita, Nov. 1, 1999, 5 pages.

Hajikazemi et al., "Chemostratigraphy of Cenomania-Turonian Carbonates of the Sarvak Formation, Southern Iran," Journal of Petroleum Geology, Apr. 1, 2012, 17 pages.

Schmid et al., "Carbon isotope stratigraphy using carbonate cements in the Triassic Sherwood Sandstone Group: Corrib Field, west of Ireland," Chemical Geology, Elsevier Science Publisher B.V. Amsterdam, vol. 225, No. 1-2, 2006, 19 pages.

Chi et al., Diagenetic history and porosity evolution of Upper Carboniferous sandstones from the Spring Valley #1 well, Maritimes Basin, Canada-implications for reservoir development, Journal of Geochemical Exploration, vol. 80, No. 2-3, Sep. 1, 2003, 21 pages.

International Search Report and Written Opinion issued in International Application No. PCT/US2018/000204 dated Dec. 13, 2018, 16 pages.

GCC Examination Report in GCC Appln. GC 2018-35837, dated Jan. 14, 2020, 4 pages.

GCC Examination Report in GCC Appln. GC 2018-35837, dated Apr. 29, 2020, 4 pages.

\* cited by examiner

IDENTIFYING OIL AND GAS RESERVOIRS WITH OXYGEN ISOTOPES

CROSS-REFERENCE TO RELATED APPLICATION(S)

This application claims the benefit of priority to U.S. Provisional Patent Application Ser. No. 62/545,637, filed on Aug. 15, 2017, the contents of which are hereby incorporated by reference.

TECHNICAL FIELD

This disclosure relates to oxygen isotope technologies, specifically to oxygen isotope technologies used to analyze rock samples.

BACKGROUND

In hydrocarbon exploration, a wellbore is formed into a geologic formation to determine the viability of hydrocarbon production from the formation. During or after the formation of the wellbore, wellbore logs and samples can be taken. A wellbore log detects various properties within the wellbore at specified depths. Future exploration and production options can be evaluated use such logs.

Petroleum reservoirs consist of various rocks including sandstones and carbonates. Geochemical analysis can help determine geological events recorded in the minerals and rocks. For example, carbon and oxygen isotopes can be used to determine depositional and diagenetic environments of carbonate rocks.

SUMMARY

This disclosure describes technologies relating to identifying oil and gas reservoirs.

An example implementation of the subject matter described within this disclosure is a method with the following features. Carbonate samples are received from a wellbore formed in a geologic formation. An oxygen isotope ratio and carbon isotope ratio present within each of the carbonate samples are determined. A mineral composition of each of the carbonate samples is determined. A plot showing the determined oxygen isotope ratios versus a depth from where within the wellbore each of the carbonate samples was obtained is created. One or more negative oxygen isotope shifts are identified based on the plot. Natural carbonate cement levels within one or more of the plurality of carbonate samples that correspond to the one or more negative oxygen isotope shifts identified in the plot are determined. One or more production sweet spots are determined based on the identified negative oxygen isotope shifts and the determined natural carbonate cement level.

Aspects of the example implementation, which can be combined with the example implementation alone or in combination, include the following. The oxygen isotope ratio and the carbon isotope ratio are determined with an isotope ratio mass spectrometer.

Aspects of the example implementation, which can be combined with the example implementation alone or in combination, include the following. Determining mineral composition includes mixing a solution comprising a red dye, potassium ferricyanaide, water, and hydrochloric acid. Thin slabs made from each of the plurality of carbonate samples are placed in the solution at 25° C. for 1-2 minutes. One or more minerals within each of the thin slabs is identified based on a degree of color change that occurs while each of the plurality of the thin slabs is in the solution.

Aspects of the example implementation, which can be combined with the example implementation alone or in combination, include the following. Substantially no color change indicates a presence of dolomite within the thin slab.

Aspects of the example implementation, which can be combined with the example implementation alone or in combination, include the following. Determining the cement levels includes visually checking porosity of one or more of the plurality of samples with a microscope.

Aspects of the example implementation, which can be combined with the example implementation alone or in combination, include the following. The samples include one sample per every one-foot interval within the wellbore.

Aspects of the example implementation, which can be combined with the example implementation alone or in combination, include the following. At least a portion of each of the plurality of samples is pulverized into a powder.

Aspects of the example implementation, which can be combined with the example implementation alone or in combination, include the following. The portion of each of the samples that is pulverized into powder produces substantially 300 micrograms of powder.

Aspects of the example implementation, which can be combined with the example implementation alone or in combination, include the following. The powder does not include cement.

Aspects of the example implementation, which can be combined with the example implementation alone or in combination, include the following. The preparation for each sample includes drying the powder at substantially 50° C. for 8-12 hours. The dried powder is transferred to a reaction vial. The reaction vial is vacuum-sealed. $H_3PO_4$ is introduced to the powdered sample. $CO_2$ gas is produced in response to introducing the $H_3PO_4$. A carbon isotope ratio and an oxygen isotope ratio are simultaneously determined in response to producing the $CO_2$ gas.

Aspects of the example implementation, which can be combined with the example implementation alone or in combination, include the following. Wellbore completion operations are at least partially planed based upon the one or more determined production sweet spots.

The details of one or more implementations of the subject matter described in this specification are set forth in the accompanying drawings and description. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
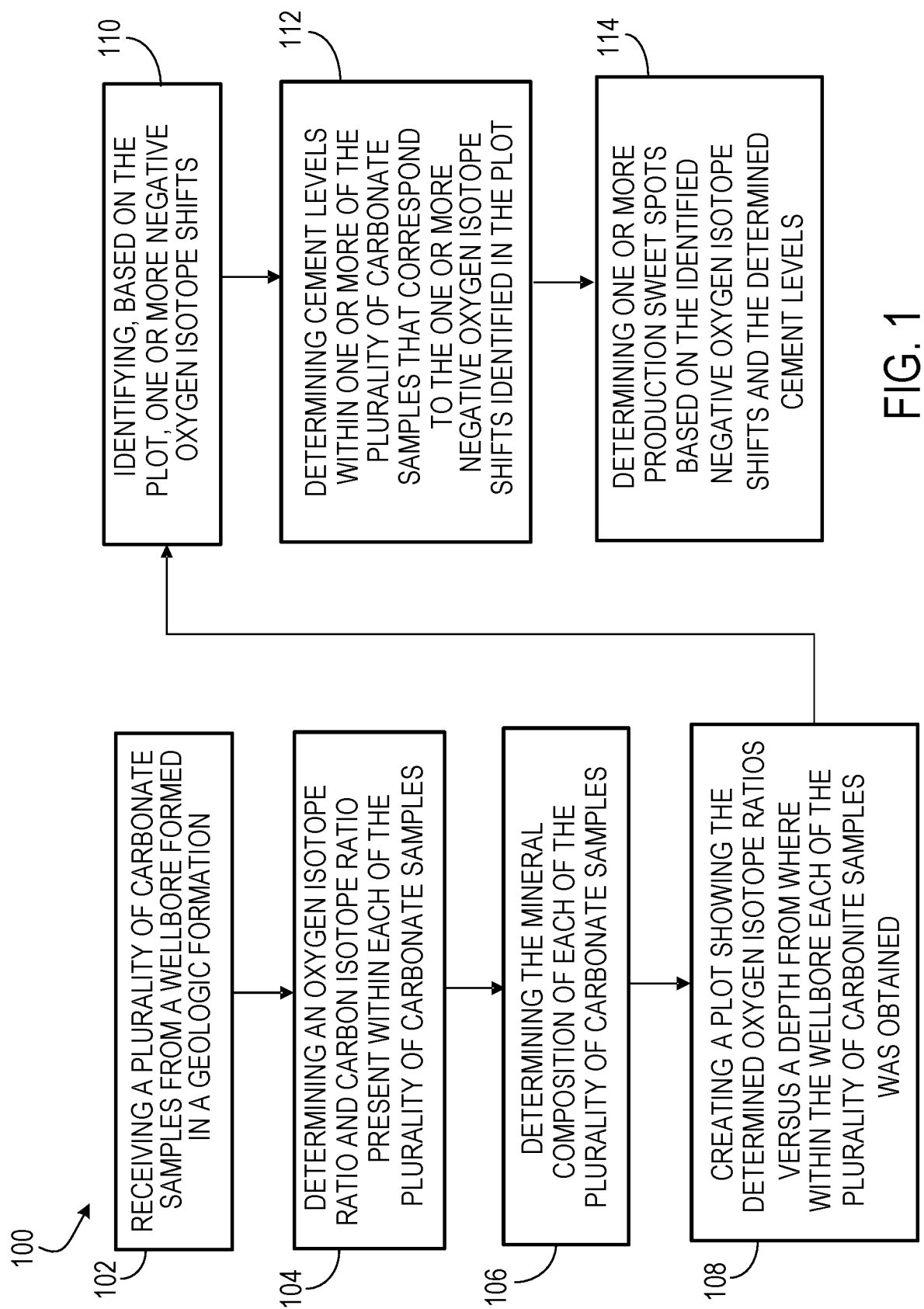
FIG. 1 is a flowchart of an example method to identify production sweet spots with oxygen isotope technologies.

During exploration operations, finding a location for a production well can be difficult. The success rate of exploratory "wildcat" wells is very small, 20% or less, even with modern advances in exploration technologies. Categorizing and developing a well properly after the wellbore has been formed can also be quite difficult.

This disclosure relates to a method for determining potential sweet spots within a reservoir based on analyzing oxygen isotopes and carbon isotopes from wellbore rock samples, such as a core sample. In the context of this disclosure, the term "sweet spot" is indicative of a petroleum enriched zone or interval. Such a zone or interval may be less than a meter or more than 100 meters in thickness. The zone or interval may also limited to one well or extend to an area or region. Elemental isotopes have the same atomic number as the rest of their element, that is, each nucleus contains the same number of protons regardless of the isotope, but different atoms of the same element can have different atomic masses due to different numbers of neutrons in the nucleus. For example, all oxygen molecules have eight protons in their nucleus, but $O^{16}$ has eight neutrons while $O^{18}$ has ten neutrons. Because of their different masses, the two isotopes behave differently during physical and chemical processes. The ratios of the two oxygen isotopes can be used to determine what kind of environments a carbonate mineral was precipitated from. While oxygen isotopes were just discussed in this example, isotopes of carbon, such as a ratio of $C^{13}$ and $C^{12}$, can be used to make similar determinations.

Carbon isotopes of carbonates are relatively stable, often with little alteration during early diagenesis in freshwater. The reason is that the carbon content within diagenetic fluids is insufficient (in contrast to oxygen) to reset the carbon within carbonates. There are a few exceptions to the stability of carbon within carbonates. One is paleo soil development, which involves biochemical reactions and generates abundant $CO_2$ that can alter the carbon isotopes in the underlying bed carbonate rocks, resulting in negative carbon isotope shift. Such a negative carbon isotope shift supports a significant diagenetic event happened. A "significant" diagenetic event will have certainly changed oxygen isotopes (negative shift). As a result, analyzing carbon isotopes can be used to help verify results determined from analyzing oxygen isotopes.

Powder is obtained from the core samples for analysis and is placed in a vial with a cap and is dried overnight. After drying the sample, the sample powders are transferred into a reaction vial capped with a septum. The oxygen and carbon isotopes from the dried sample are analyzed and compared with standards, such as NBS-19 and NBS-18, and are recorded. These are several pure carbonate international standards with known carbon and oxygen isotope values, and they are provided by recognized standard institutes, such as the International Atomic Energy Agency (IAEA) and the United States Geological Survey (USGS). The typical practice in an isotope laboratory to analyze isotopes in carbonates is to prepare a set of carbonates, for example, 10, 50 or 100 carbonate samples. The set can include of 2-3 different standards.

The standards and samples go through the same processes including preparation, treatment and analysis. The carbon and oxygen isotopes of standards are known values, whereas the carbon and oxygen isotopes of samples are to be determined based on the known isotope values. That is, the carbon and oxygen isotopes of the samples are calculated automatically based on the carbon and oxygen isotopes of the standards by the mass spectrometer's software during the analysis.

The oxygen isotope ratio for each sample is plotted versus the depth of the reservoir formation from which each of the samples was obtained. Outstanding negative oxygen isotope shifts are identified as potential reservoirs, or "sweet spots". The negative shift can be either a sudden or a gradual one. If all the profile has substantially consistently similar isotope values, a negative shift even a small shift, such as −1 permil may be outstanding. However, if the whole profile has an oxygen isotope variation, a larger negative shift, such as, 2-3 permil or more, may be needed to call a negative shift/ reservoir potential. Such a shift of that magnitude can look like a gradual shift, rather than a sudden one. In general, an "outstanding" shift is relative to background data. For instance, if a set of background data has little variation (plotted like a straight line), then a small spike from one interval (1‰ or less) appears outstanding. If the set of background data has a large variation (for example, a change from −2 to +2), then any "outstanding" would have to be a much larger spike (for instance, more than 3 permil) to be outstanding from the background Once negative oxygen isotopes are identified, make sure that the negative isotope shifts are not result of intervals or zones with abundant natural carbonate cements. Then we may conclude that there is potentially significant porosity and a sweet spot corresponding to the negative isotope shifts. Throughout this disclosure, all references to "cement" refer to naturally occurring carbonate cement within the geological formation unless otherwise specified. In the context of this disclosure, a "sweet spot" is an interval or bed of a geologic formation that has a greater likelihood of producing hydrocarbons. A final check can include examining the core sample under a microscope for diagenesis and visible porosity. Using these techniques to identify sweet spots can increase the identification rate of successful exploratory wells.

In some implementations, aspects of this disclosure can be performed during real-time operations, that is, while the drilling operations are being implemented. For example, a drill bit can be steered towards one or more identified/ detected sweet spots and away from less promising parts of the formation based on results of the oxygen isotope analysis. In addition, the results taken from aspects of this disclosure can be input into a geologic model and can be used to predict other potential sweet spots within the field. In some implementations, oxygen isotopes can be measured in real-time while well is being drilled. In such an implementation, portable instruments can be deployed in the field. The great benefit of the real-time measurement is that the drilling operation may stop after penetrating the targeted reservoir bed and focus on the next phase of exploration or production.

FIG. 1 is a flowchart of an example of a method 100 that can be implemented according to aspects of this disclosure. At 102, multiple carbonate samples are received from a wellbore formed in a geologic formation. In some implementations, the samples can include one sample per every one-foot interval within the wellbore. Samples can be taken at different intervals depending on the desired granularity of the test results and the specific geologic conditions of each individual well. For example, a sample can be taken every foot or once every ten meters. Samples can include core samples, or any other sample containing carbonate from the specified well interval. There is no strict requirements on dimension or weight for each sample. For example, milligrams can be enough. However, large samples will allow the determination if a portion of the sample is representative of the interval, or just an abnormal part. Only the former shall be collected and examined. In some implementations, the samples can be obtained after the wellbore has been formed. In some implementations, the samples can be obtained during drilling operations. Both obtaining samples during or after drilling operations yield similar results. In some implementations, an auger is used to break rocks into chips/debris which will cycling up to the surface with drilling fluids. In some implementations, a sampling tube is used to take a core sample. For example, a sample tube with a diameter of two or four inches can be used to obtain a continuous sample for the whole well. Cored samples are commonly sealed to preserve proper moisture. For cored large chunks of rock samples, if samples are not cleaned during drilling, they can be cleaned prior to testing. For example, a piece of hard rock with traces of dried drilling muds can be rinsed with clean water and dried prior to testing.

At 104, an oxygen isotope ratio and carbon isotope ratio present within each of the carbonate samples are determined. In some implementations, the oxygen isotope ratio and the carbon isotope ratio are determined with an isotope ratio mass spectrometer. In such an implementation, at least a portion of each of the samples is pulverized into substantially 300 micrograms of powder. For example, 250-350 micrograms can be used. In some implementations, large natural cement fragments, fossil fragments, or both, are avoided during powder collection. "Large" in this context indicates that the fragment is large enough to see with the naked-eye or microscope and be avoided by sampling bits. More details on what constitutes natural cement will be discussed later within this disclosure. When a rock sample is collected, a matrix of the rock sample can include primarily deposited components, altered crystals, and cements. The cements and altered crystals can create a negative shift. Diagenetic cements vary from millimeter to centimeters. One small piece of rock may consist of mainly primary minerals but with one large cement in a pore area. If a technician only collects the cement, then tests will result in a large negative shift that may not be representative of the real rocks from the interval. On the other hand, a sample with a large fossil fragment can skew results as well. In such an instance, the large cements and fossil fragments are avoided as they can alter a portion in matrix and can yield inaccurate results.

Once the powder for each sample is formed, the multiple powdered samples are prepared for testing. Each sample is marked so that it can be mapped to the depth within the wellbore from which each sample was obtained. The powder is dried prior to testing at substantially 50° C. (plus or minus 10° C. for substantially 8-12 hours (for example, overnight)). After drying, the dried powder is transferred to a reaction vial that includes a septum. The reaction vial is vacuum-sealed through the septum after it receives the powder. Phosphoric acid ($H_3PO_4$) is introduced to the powdered sample. In some implementations, the phosphoric acid is introduced to the powder through the septum. In such an implementation, the vials with carbonate powder and acid are included in a closed-temperature device. After a period of time (for example, 12 hours), the reaction of powder and acid is completed and $CO_2$ is released and sucked into another tube connected to mass spectrometer. In some implementations, four to six drops of $H_3PO_4$ at 100% by mass or greater concentration can be used. The isotope ratios of both carbon and oxygen in the $CO_2$ gas of samples are simultaneously analyzed and calibrated based on the isotope ratios of $CO_2$ gases produced from a set of standards, such as NBS-19 and NBS-18, the international carbonate standards, or laboratory standards that are prepared and calibrated with international standards.

At 106, the mineral composition of each of the carbonate samples is determined. In some implementations, for quick results, identifying the mineral composition can include mixing a solution comprising a red dye, such as Alizarin Red S, potassium ferricyanaide, water, and hydrochloric acid. In some implementations, another dye besides Alizarin Red S can be used. Thin slabs made from each of the carbonate samples is then placed in the solution at room temperature, for example, 25° C., for 1-2 minutes. If the ambient temperature is greater, the dying effect will occur more quickly. One or more minerals within each of the thin slabs can be identified based on a degree of color change that occurs while each of the thin slabs is in the solution. For example, substantially no color change indicates a presence of dolomite within the thin slab. Calcite reacts more quickly to the acid and dye mixture than dolomite. While submerged in the mixture, dolomite will not react with the solution and stay unaffected in a few minutes. For the purposes of the dye test previously described, the thickness of the slab does not matter as long as the surface of it contains all representative minerals. Aragonite and calcite will change color, dolomite will not.

Figure 2A:
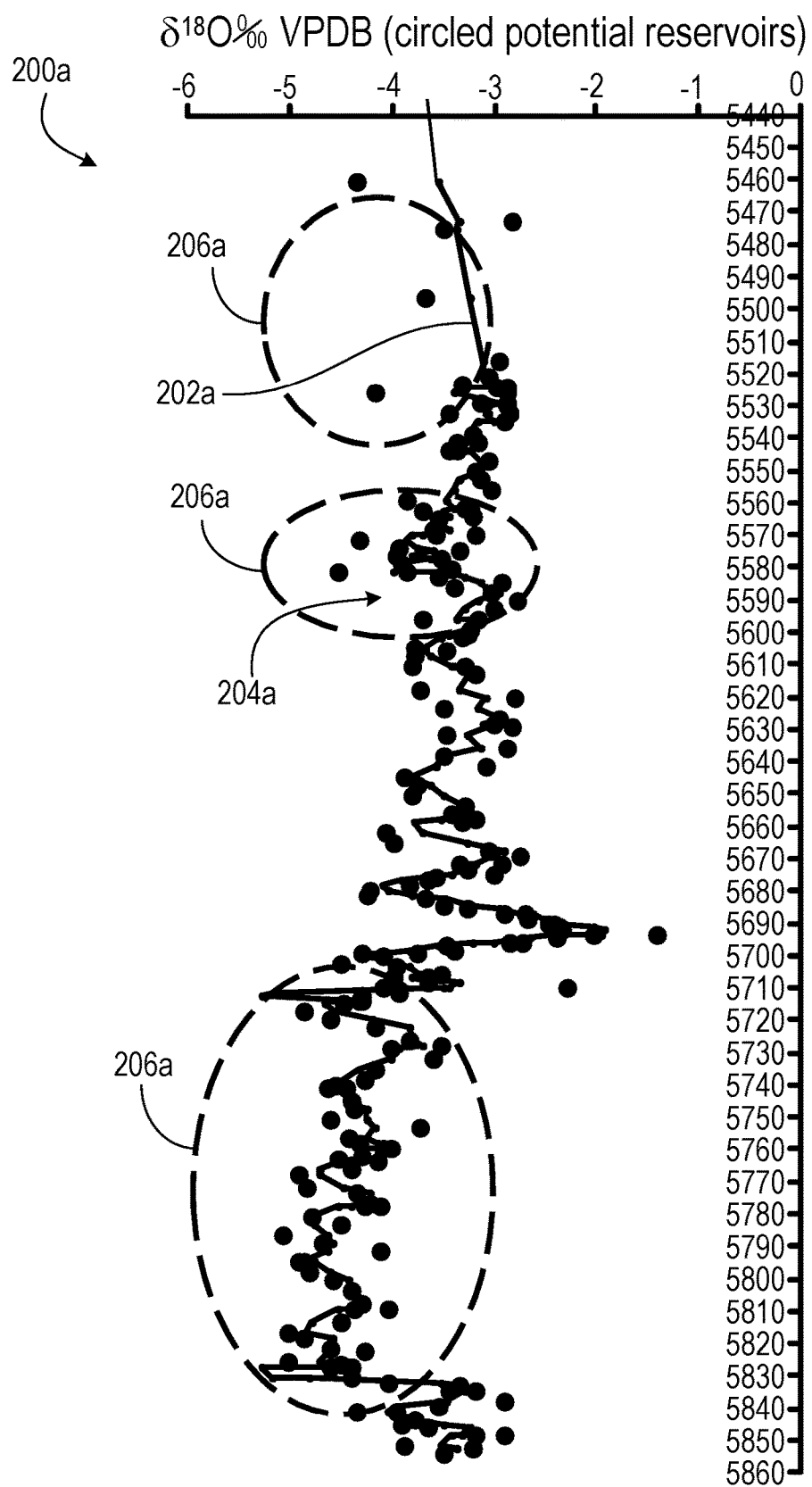
FIGS. 2A-2B are example plots that can be used to identify production sweet spots.

At 108, a plot showing the determined oxygen isotope ratios versus a depth from where within the wellbore each of the carbonite samples was obtained is created. FIG. 2A is an example of such a plot. The X-axis shows an isotope ratio of a carbonate sample while the Y-axis shows a depth from which the sample was obtained. The magnitude for any recognizable shift depends on the background. If the background is near a straight/flat line, such as section 202a, 1‰ is enough to show a shift. However, if the background has a variation of (+/−) 2‰, such as section 204a, at least a 3‰ variation may be indicative of a shift.

At 110, one or more negative oxygen isotope shifts are identified based on the plot, such as the plot illustrated in FIG. 2A. The circled areas 206a in the FIG. 2A indicate potential sweet spots for production. However, other factors can play into the production viability of the highlighted areas. The negative shift (shown as the line moving left in FIG. 2A) can be an either sudden or gradual one, that is, the isotope values less than the general background values. If all the profile has pretty consistent isotope values, one interval shows a negative shift even a small shift, such as −1‰, can be called a severe shift. However, if the whole profile has an oxygen isotope variation such as about 1-2‰, a larger negative shift, such as, 2-3‰ or more, may be needed to call a negative shift/reservoir potential, even if the shift occurs gradually.

Figure 2B:
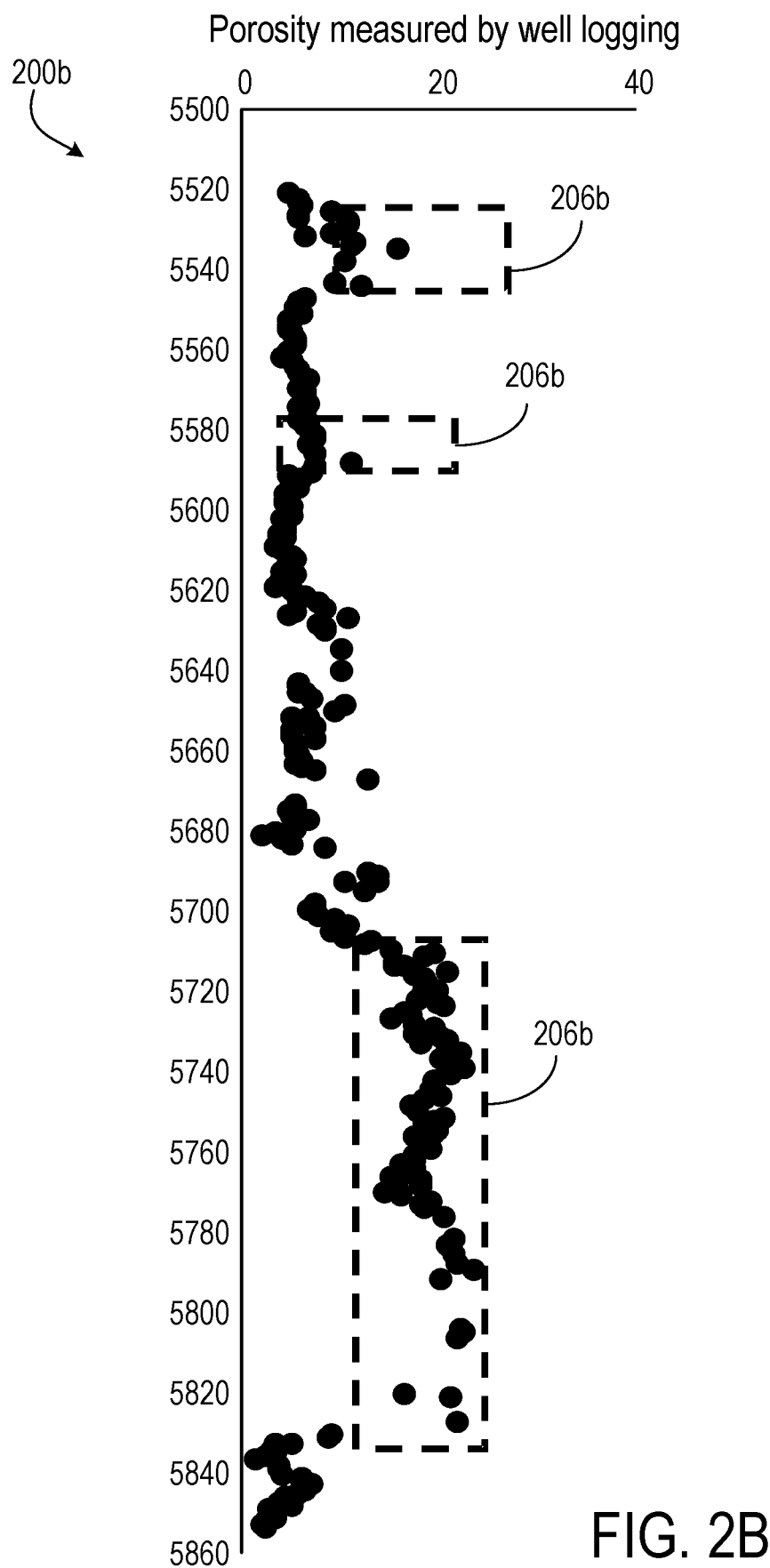

At 112, cement levels within one or more of the carbonate samples that correspond to the one or more negative oxygen isotope shifts identified in the plot are determined. The relationship between cements and porosity is dependent upon several factors within the formation. In some instances, more cements can mean less porosity, but no cements at all implies that no diagenesis has occurred. Lack of diagenesis means that no secondary porosity is formed. Carbonate cementation involves ions carried in groundwater chemically precipitating to form new carbonate minerals between sedimentary grains. So cement is typical a freshwater diagenetic product. The significance here is that cement presence itself indicates diagenesis occurred in the rocks. Typical freshwater diagenesis will dissolve instable minerals (partially or completely) to produce porosity. However, the porosity can be refilled partially or completely by cement. The most common situation is one pore or void is filled by a large cement. Comparing to matrix of rocks, the cement can appear clean/clear and large (crystal), so it can be recognized from hand samples by naked eyes, small hand lens, and/or microscopic observation. In some implementations, determining the cement levels can include visually checking porosity of one or more of the samples with a microscope. Such observations can be corroborated with porosity measurements from a standard well log, such as the log 200b shown in FIG. 2B. The X-axis shows a porosity of the sample while the Y-axis shows a depth from which each sample was obtained. The boxed areas 206b in the FIG. 2B indicate potential sweet spots for production as there are increases (rightward shift as shown in FIG. 2B) in porosity at the highlighted depths. The porosity log can be can be confirmed using density logging, neutron porosity logging, sonic logging, or any other logging technique useful for determining porosity.

At 114, one or more production sweet spots are determined based on the identified negative oxygen isotope shifts and the determined cement levels. That is, after determining no significant amounts of carbonate cements, the intervals with a significant negative shift, are potentially of significant porosity, and potential sweet spots for production. After examination, if too much cement is observed, then there might be insufficient porosity to allow for production.

Wellbore completion operations can be planned at least partially based upon the one or more determined production sweet spots. For example, for each well, a target depth can be at least partially determined for drilling and completion operations. In one example, a significant potential for production within a first interval in the targeted formation from well "A" has determined. In this example, petroleum is known to be produced from the targeted formation in this and adjacent basins. Well "A" and any wells adjacent to well "A" will very likely encounter petroleum if being drilled into the determined target interval of the targeted formation. In some implementations, a similar analysis of multiple wells in a basin can be used to build or improve a reservoir model. The subject matter can also be used to determine information about the basin as the result can be projected to all directions, for example, basin direction, margin direction, or 90 degrees toward basin direction. The distance from the wellbore that the results are valid depends on the specific characteristics of the basin and formation. Also, the application may be either live, that is, sampling and analyzing during drilling operations, or sampling and analyzing later, after drilling operations. In some implementations, the two methods can be combined. For example, after cored samples have been analyzed, real-time analyzing may be conducted for new wells within the same basin during drilling operations.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

The invention claimed is:

1. A method comprising:
receiving a plurality of carbonate samples from a wellbore formed in a geologic formation;
determining an oxygen isotope ratio and carbon isotope ratio present within each of the plurality of carbonate samples;
determining a mineral composition of each of the plurality of carbonate samples;
mixing a solution comprising a red dye, potassium ferricyanaide, water, and hydrochloric acid;
placing thin slabs made from each of the plurality of carbonate samples in the solution at 25° C. for 1-2 minutes;
identifying one or more minerals within each of the thin slabs based on a degree of color change that occurs while each of the plurality of the thin slabs is in the solution;
creating a plot showing the determined oxygen isotope ratios versus a depth from where within the wellbore each of the plurality of carbonate samples was obtained;
identifying, based on the plot, one or more negative oxygen isotope shifts;
determining natural carbonate cement levels within one or more of the plurality of carbonate samples that correspond to the one or more negative oxygen isotope shifts identified in the plot; and
determining one or more production sweet spots based on the identified negative oxygen isotope shifts and the determined natural carbonate cement levels.

2. The method of claim 1, wherein the oxygen isotope ratio and the carbon isotope ratio is determined with an isotope ratio mass spectrometer.

3. The method of claim 1, wherein substantially no color change indicates a presence of dolomite within the thin slab.

4. The method of claim 1, wherein determining the natural carbonate cement levels comprises visually checking porosity of one or more of the plurality of samples with a microscope.

5. The method of claim 1, wherein the plurality of samples comprises one sample per every one-foot interval within the wellbore.

6. The method of claim 1, further comprising pulverizing at least a portion of each of the plurality of samples into a powder.

7. The method of claim 6, wherein the portion of each of the plurality of samples that is pulverized into powder produces substantially 300 micrograms of powder.

8. The method of claim 6, wherein the powder does not include cement.

9. The method of claim 6, further comprising preparing the powdered samples, the preparation for each sample comprising:
drying the powder at substantially 50° C. for substantially 8-12 hours;
transferring the dried powder to a reaction vial;
vacuum-sealing the reaction vial;
introducing $H_3PO_4$ to the powdered sample;
producing $CO_2$ gas in response to introducing the $H_3PO_4$; and
determining a carbon isotope ratio and an oxygen isotope ratio simultaneously in response to producing the $CO_2$ gas.

10. The method of claim 1, further comprising planning wellbore completion operations at least partially based upon the one or more determined production sweet spots.

11. The method of claim 1, further comprising:
comparing the determined oxygen isotope ratios and the determined carbon isotope ratios; and
verifying the determined oxygen isotope ratios based on the comparison.

* * * * *